(12) United States Patent
Meunier et al.

(10) Patent No.: US 11,931,298 B2
(45) Date of Patent: Mar. 19, 2024

(54) EYEWEAR WITH VARIABLE COMPRESSION CUSHION AND IMPROVED MOISTURE MANAGEMENT

(71) Applicant: Oakley, Inc., Foothill Ranch, CA (US)

(72) Inventors: Benjamin John Meunier, San Clemente, CA (US); Dugan O'Keene, Newport Beach, CA (US); Ryan Neil Saylor, Mission Viejo, CA (US); Cameron Scott Burns, Rancho Santa Margarita, CA (US)

(73) Assignee: Oakley, Inc., Foothill Ranch, CA (US)

( * ) Notice: Subject to any disclaimer, the term of this patent is extended or adjusted under 35 U.S.C. 154(b) by 0 days.

(21) Appl. No.: 17/031,068

(22) Filed: Sep. 24, 2020

(65) Prior Publication Data
US 2021/0106464 A1    Apr. 15, 2021

Related U.S. Application Data

(60) Provisional application No. 62/915,362, filed on Oct. 15, 2019.

(51) Int. Cl.
*A61F 9/02*    (2006.01)

(52) U.S. Cl.
CPC .............. *A61F 9/026* (2013.01); *A61F 9/028* (2013.01); *A61F 9/029* (2013.01)

(58) Field of Classification Search
CPC .. A61F 9/02; A61F 9/026; A61F 9/028; A61F 9/029
See application file for complete search history.

(56) References Cited

U.S. PATENT DOCUMENTS

| | | | |
|---|---|---|---|
| 9,642,749 B2 * | 5/2017 | McNeal | G02C 5/122 |
| 2004/0181858 A1 | 9/2004 | Soto et al. | |
| 2011/0088150 A1 | 4/2011 | Tominaga et al. | |
| 2013/0067626 A1 | 3/2013 | Sandor | |
| 2014/0115761 A1 | 5/2014 | McNeal et al. | |
| 2016/0158064 A1 * | 6/2016 | Favre-Felix | A61F 9/026 2/431 |

(Continued)

FOREIGN PATENT DOCUMENTS

| | | |
|---|---|---|
| JP | 2011083539 A | 4/2011 |
| KR | 2020100008720 U | 9/2010 |

OTHER PUBLICATIONS

International Search Report and Written Opinion, dated Nov. 16, 2020 in Related PCT Application No. PCT/US2020/052454; 11 pages.

*Primary Examiner* — F Griffin Hall
(74) *Attorney, Agent, or Firm* — Sterne, Kessler, Goldstein & Fox P.L.L.C.

(57) ABSTRACT

A variable compression cushion for eyewear includes a lattice structure made up of lattice cells defined by lattice elements. The parameters of the lattice structure may be configured to create a desired compressibility in the cushion. Different zones of the cushion may have different compressibility. The variable compressibility enables the cushion to be configured to optimize the face pressure experienced by a user when the eyewear is worn to enhance the comfort of the user. Some embodiments of the cushion also include structures to improve ventilation through the cushion. Some embodiments of the cushion also include structures that channel moisture away from the portion of the cushion that contacts the face of the user to improve user comfort.

32 Claims, 10 Drawing Sheets

(56) References Cited

U.S. PATENT DOCUMENTS

2017/0290706 A1* 10/2017 Chiang ................ A63B 33/004
2018/0264718 A1* 9/2018 McCluskey ............ B33Y 40/00
2018/0341286 A1* 11/2018 Markovsky ............ A42B 3/127

* cited by examiner

EYEWEAR WITH VARIABLE COMPRESSION CUSHION AND IMPROVED MOISTURE MANAGEMENT

BACKGROUND

Eyewear is often worn for extended periods of time, particularly in situations where the eyes must be protected from flying debris or inclement weather. Eyewear is typically worn in contact with the face of a user and must fit the face comfortably, especially in situations where the eyewear is worn for extended periods of time. This is particularly important for eyewear that has more face contact or that requires a more secure fit. For example, many goggles employ a cushion on the interior side of the goggle that contacts the face and forms a complete loop on the interior surface of the goggle. The cushion of a goggle typically contacts a significant area of the user's face.

Goggles are usually secured using a flexible strap that loops around the rear of the head of the user. The strap pulls the goggle backwards onto the user's face, which the user experiences as pressure along the cushion. As the goggle strap is tightened for a more secure fit, the pressure felt by the user increases. After a certain point the pressure will reach an uncomfortable point, especially if the goggle needs to be worn for an extended period of time. Existing goggle cushions are usually made of a foam material that compresses when pressed against the user's face to increase comfort as the goggle strap is tightened. A face pressure considered comfortable by the user may vary with the contact location. For example, a comfortable face pressure on the brow may be different than a comfortable pressure on the cheek. Another aspect of a comfortable fit is moisture management. A cushion that absorbs moisture and remains damp can be uncomfortable for a user. Also, warmer, humid air in the captured space between the eyewear lens and face can result in increased lens fogging if that space lacks proper ventilation. Further improvements in face pressure and moisture management are needed to enhance user comfort while wearing eyewear.

BRIEF SUMMARY

Embodiments of an eyewear cushion according to the present disclosure include variable compressibility features that allow a face pressure to differ at different points in the cushion. This allows the feel of the cushion to be optimized for the user. Also disclosed are cushions that provide the eyewear with improved moisture management for better comfort and performance. Some embodiments of the present disclosure are a goggle including a cushion having a first surface and a second surface opposite the first surface, the second surface of the cushion opposite the first surface is configured to follow a contour of a face of a user when the goggle is being worn. The cushion has a first zone with a first compressibility and a second zone with a second compressibility that is less than the first compressibility.

Further embodiments of the present disclosure are a goggle a cushion having a first surface and a second surface of the cushion that is opposite the first surface and that is configured to follow a contour of a face of a user when the goggle is being worn. The cushion can comprise an additively manufactured, continuous and uninterrupted lattice structure. The cushion is configured to create a first pressure on the face of the user in a first zone when the goggle is being worn, and create a second pressure on the face of the user in a second zone separate from the first zone when the goggle is being worn. The second pressure can be different from the first pressure.

Further embodiments of a cushion for a goggle include a continuous and uninterrupted lattice structure comprising a plurality of lattice cells, a first surface configured to mate with a portion of the goggle, and a second surface opposite the first surface. First and second compression forces required to compress the lattice structure by a same distance at first and second points, respectively, on the second surface can be different, where the first and second compression forces are measured in a direction extending between the first surface and the second surface.

BRIEF DESCRIPTION OF THE DRAWINGS/FIGURES

DETAILED DESCRIPTION

Figure 1:
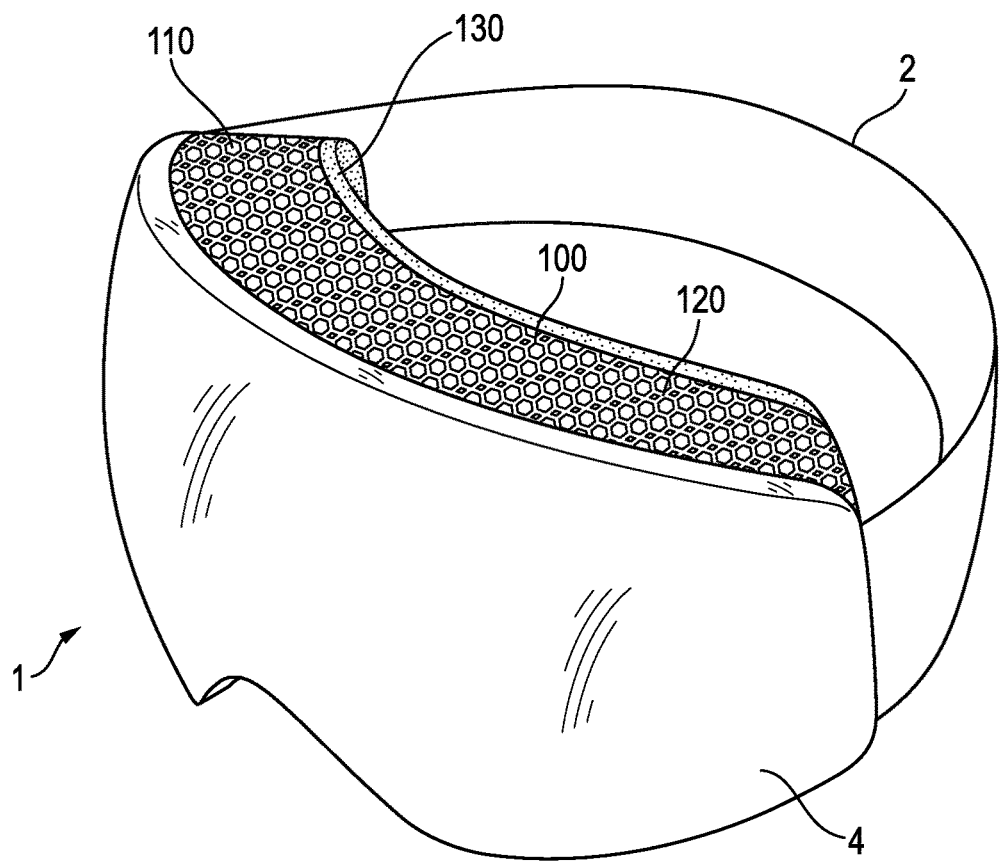
FIG. 1 is a perspective view of a goggle including a goggle cushion according to embodiments.

Embodiments of the present invention(s) will now be described in detail in the accompanying drawings. References to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As discussed in the Background, cushions are used in eyewear, particularly in goggles, to increase comfort of a user in regions where the eyewear contacts the face of the user. Designing a cushion for eyewear requires balancing several different design requirements. The cushion must deform enough to make the eyewear comfortable to wear. However, the cushion must also be resilient or stiff enough to ensure that it does not "bottom out" or compress so far to allow the user to feel a hard portion of the eyewear against their face. Cushions must also be designed to hold the eyewear the desired distance from the face when worn.

With reference to a cushion for a goggle where the cushion contacts a significant area of the user's face, achieving a comfortable goggle fit results in variable face pressure in different regions of the face. Given that the rearward pressure on the goggle caused by the strap is constant, the compressibility of the cushion may be varied to achieve variable face pressure. Generally, a softer, e.g., more compressible, cushion will result in less face pressure when deflected a given distance. A stiffer, e.g., less compressible, cushion will result in greater face pressure when deflected the same given distance. However, known cushions have a constant compressibility. When worn, some areas of goggle cushions are compressed more than other areas, which when coupled with a cushion with constant compressibility, results in a greater compression force on the face of a goggle wearer. This can make known cushions uncomfortable to wear because of the higher face pressure in areas of greater compression. However, with a variable compression cushion, it is possible to tailor the face pressure experienced by the user to a desired pressure profile. Thus, a variable compression cushion goggle can allow for a more secure fit—with a tighter goggle strap—at the same comfort level along the entire contact surface on the wearer's face.

In some embodiments, a variable compression cushion may be made from a single continuous portion. In other embodiments a variable compression cushion may be made from cushion portions of different relative compressibility that have been joined together. For example, the aesthetics of a cushion can be a consideration, and simply joining existing cushion portions together may not be aesthetically acceptable because of the visual differences between the cushion portions. Moreover, moisture management of existing cushion portions may be challenging in some situations.

An embodiment of the present disclosure is a goggle with a cushion attachment region and a cushion having a first surface and a second surface opposite the first surface. The second surface of the cushion opposite the first surface is configured to follow a contour of a face of the user. The cushion has a first zone with a first compressibility and a second zone with a second compressibility that is greater than the first compressibility.

Advantages of this and other embodiments include, for example, the ability to tailor the face pressure experienced by the user to optimal amounts by designing the cushion with different compressibility in the first, second, and further zones as desired depending on design goals. Optimal amounts of face pressure may vary at different points or in different zones of the user as discussed below. Further advantages of this and other embodiments are also discussed below.

As shown in FIGS. 1-4, a goggle 1 includes a lens 4 and a strap 2 attached to the left and right ends of lens 4. Strap 2 is attached to lens 4 such that it forms a loop configured to encircle the head of a user. Strap 2 may be constructed from a soft, elastic material and may include adjustment elements to adjust the length of strap 2. Lens 4 is configured to allow a user to see through lens 4 and may be constructed from any suitable material that is substantially transparent, such as plastic materials or glass materials. In embodiments such as those shown in FIGS. 1-4, goggle 1 does not include a frame and, accordingly, lens 4 is designed with sufficient structural rigidity to serve as the main structural support of goggle 1. Further, the lack of a frame means that lens 4 may include attachment points for strap 2. However, cushion 100 may also be used with embodiments of goggle 1 that include a frame.

Figure 2:
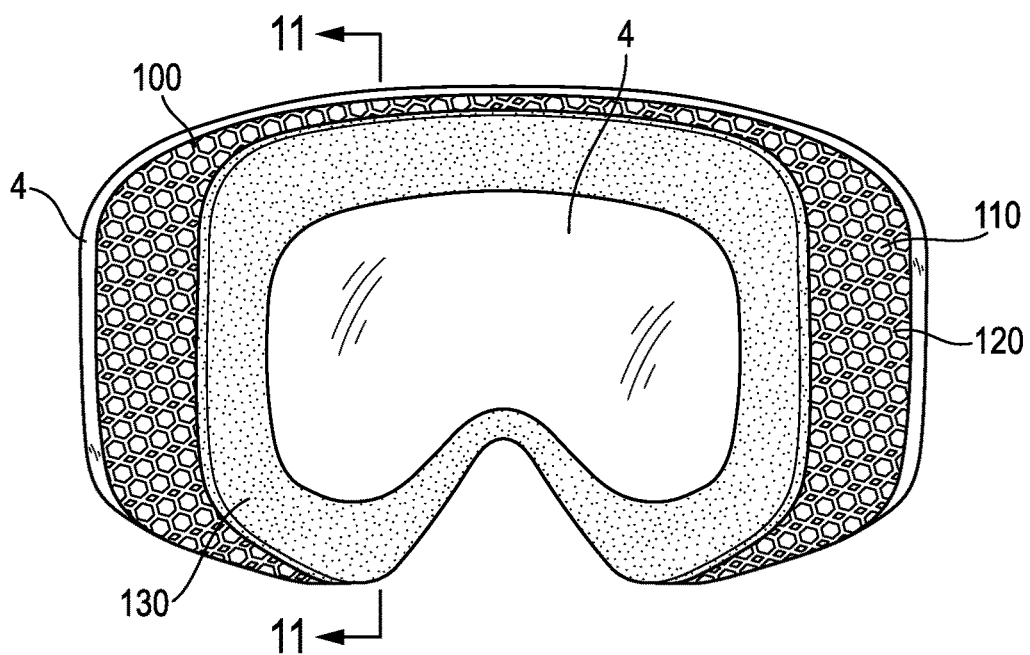
FIG. 2 is a rear view of the goggle of FIG. 1, according to embodiments.

In frameless embodiments of goggle 1, a cushion 100 is attached to the interior surface of lens 4. As best shown in FIG. 2, in embodiments cushion 100 may form an enclosed loop on the interior of lens 4 by encircling the perimeter of lens 4. Cushion 100 may also be discontinuous, for example, cushion 100 may only partially extend along the perimeter of lens 4. In such embodiments with discontinuous cushions, cushion 100 may extend from a side of the goggle to a laterally opposite side along the upper or lower perimeter of the lens. Therefore, cushion 100 can be disposed only along the top brow region of the goggle or along the bottom cheek region of the goggle. Cushion 100 is contoured to follow the face shape of a user when goggle 1 is worn. Cushion 100 comprises a continuous and uninterrupted lattice structure that includes lattice cells 110 defined by lattice elements 120. An enlarged view of a portion of cushion 100 with single lattice cell 100 and corresponding lattice elements 120 is shown in FIG. 5a. Lattice cells 110 are the cells, e.g., openings, that make up cushion 100. Lattice elements 120 are the elements, e.g., walls, that define the shape of the lattice cells 110. Thus, in FIG. 5a, the single lattice cell 110 is shown as a hexagon shaped cell, and lattice elements 120 are visible and form the six sides of the exemplary lattice cell 110. Lattice elements 120 are made of an elastically deformable material. In some embodiments, lattice elements 120 may have a circular cross section when viewed in a plane perpendicular to the axis of lattice elements 120 (i.e. lattice elements 120 may be cylindrically shaped).

In embodiments, cushion 100 may comprise a face layer 130 attached to a second surface 104 of cushion 100 that is opposite a first surface 102 of cushion 100. Face layer 130 may be attached using any suitable method, including adhesives. First surface 102 is configured to attach to goggle 1, and second surface 104 is therefore the surface of cushion 100 that is closer to the user's face. Face layer 130 may be a thin layer of material configured to increase comfort of the user when cushion 100 is being worn. As shown in FIGS. 3-6, face layer 130 is configured to contact the face of the user and may entirely cover second surface 104 of cushion 100. In some embodiments, the lattice structure of cushion 100 is at least twice the thickness of face layer 130. Face layer 130 may be made of any suitable soft material such as foam, felt fabric, or other fabrics.

Figure 5:
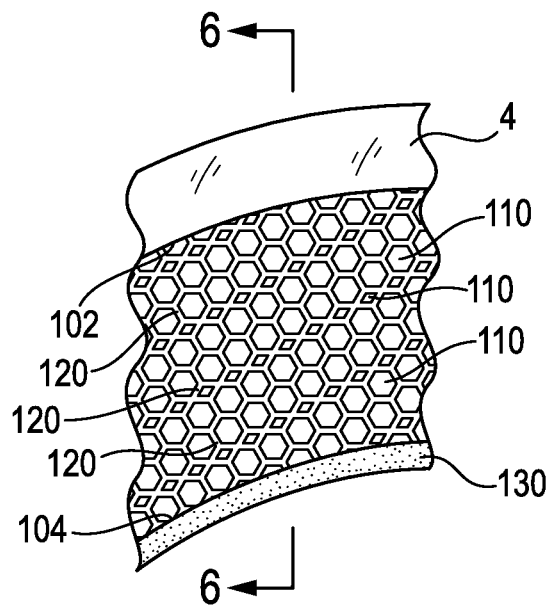
FIG. 5 is a top view of a portion of the goggle cushion of FIG. 1 according to embodiments.
Figure 5A:
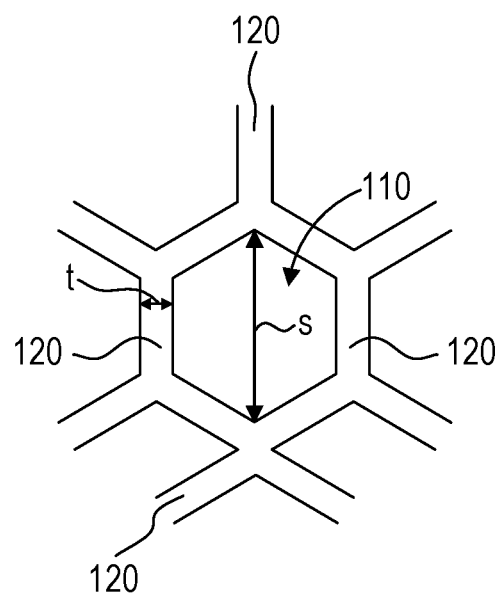
FIG. 5a is a detail view of the goggle cushion of FIG. 5, according to embodiments.
Figure 6:
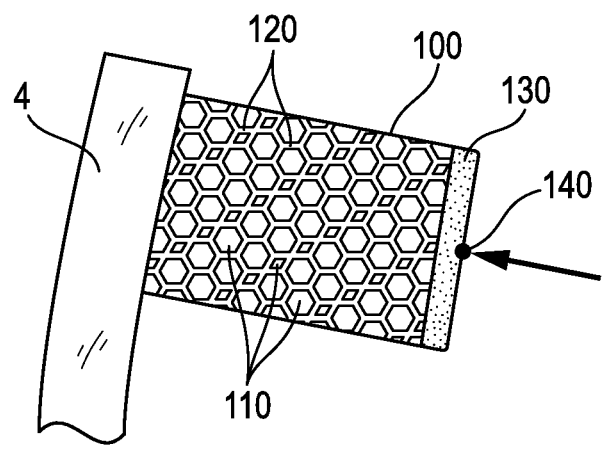
FIG. 6 is a cross-section view of the goggle cushion along line 6-6 of FIG. 5.

As best shown in FIGS. 5 and 6, lattice cells 110 and lattice elements 120 extend throughout cushion 100. Lattice cells 110 may be designed in any desired configuration. For example, lattice cells 110 may be configured with a regular, repeating crystalline structure such as a body centered cubic structure, face centered cubic structure, hexagonal structure, monoclinic structure, or tetragonal structure. Alternatively, lattice cells 110 may be any desired repeating structure, such as spheres, cones, cylinders, pyramids, prisms, or any other round, polygonal, or irregular shape, or may be configured with a varying or random structure throughout cushion 100. Lattice cells 110 can be part of a continuous structure that extends throughout cushion 100 (i.e. entire cushion 100 is formed of lattice cells 100) and that is not interrupted or otherwise made of discontinuous materials. For example, cushion 100 is not manufactured from different materials that are adhered, welded, or otherwise attached together. Instead, cushion 100 can consist of one continuous lattice structure.

The dimensions of lattice cells 110 and lattice elements 120 may be varied as desired, as discussed in further detail below. For example, as shown in FIG. 5a, lattice cells 110 may be configured in a hexagonal structure that has a size s of about 8 mm per side, with lattice elements 120 having a thickness t between about 0.60 mm to about 0.80 mm. In other embodiments, lattice cells 110 may be configured in a stochastic (i.e. random) pattern with an approximate cell size s of about 5 mm, with lattice elements 120 having a thickness t between about 0.70 mm to about 1.0 mm. The lattice structure of cushion 100 may be made using any suitable manufacturing technique. For example, cushion 100 may be made using additive manufacturing techniques, often called "3D printing" techniques. Any suitable elastically deformable material may be selected for lattice elements 120. Preferably, the material selected is easy to adapt to additive manufacturing processes and is resistant to environmental degradation from weather, temperature, or UV exposure. Suitable materials include, for example and without limitation, plastics (e.g., elastomerics, such as those well-suited for lattices needing high resiliency) and rubber materials. In some embodiments, cushion 100, and specifically lattice elements 120, is not made of materials traditionally used in standard foam cushions, such as polyurethane, EVA, or neoprene foams.

Compressibility can be expressed as the force needed to compress a material a set distance, and can be discussed in terms of the "spring force constant" defined in Hooke's Law: $F=k*x$, where "F" is the force needed, "x" is the set distance, and "k" is the spring constant. For purposes of this application, the compressibility of cushion 100 will be measured by having a force applied perpendicularly to second surface 104, as best shown by the direction indicated by the arrow in FIG. 6. A first location 140 is shown where the arrow meets cushion 100 to illustrate where the compression force is applied. It should be understood that the compressibility may be measured using a force distributed over a known area at first location 140, for example, applying a force over 1 cm² or 1 in² of cushion 100 to compress a certain distance. Compressibility at first location 140 may also be measured at one point at location 140. For purposes of this application, compressibility may be expressed as a relative compressibility between different zones of a cushion or different cushions, in terms of the force needed to compress such cushions or zones thereof by the same set distance, i.e., how difficult it is to compress a cushion by such set distance. Thus, a higher compressibility zone refers to a zone of cushion 100 being easier to compress than another lower compressibility zone of cushion 100 by the same set distance. Since the set distance is the same and not varied in relative compressibility measurements, the spring force constant expresses the same phenomenon as compressibility, but in a numerically opposite fashion: a higher spring force constant cushion 100 has a lower compressibility, e.g., it is more difficult to compress, or stiffer. Both "compressibility" and "spring force" or "spring force constant" will be used throughout this specification to refer to how much force it takes to compress cushion 100 by a given set distance.

The design of the lattice structure of cushion 100, including, for example, the configuration of lattice cells 110, the dimensions of lattice cells 110, the dimensions of lattice elements 120, and the materials chosen for lattice elements 120 may be varied to achieve a desired compressibility of cushion 100. For example, holding all other parameters constant, using lattice elements 120 with a greater thickness t will generally decrease the compressibility of cushion 100, while using lattice elements 120 with a smaller thickness t will increase the compressibility. Likewise, choosing lattice cells 110 with a smaller size s, which results in closer packing of lattice cells 110, will generally result in a lower compressibility. Material choice also affects the compressibility, with stronger materials generally resulting in a lower compressibility. This variability of compression differs from a standard foam cushion known in the art because a standard foam cushion with a constant nominal compressibility (i.e., lacking variable compressibility) will also apply different face pressures at different areas, but by virtue of the foam cushion becoming more compressed (i.e., deflected by a greater distance) in one area compared to another area.

Figure 7:
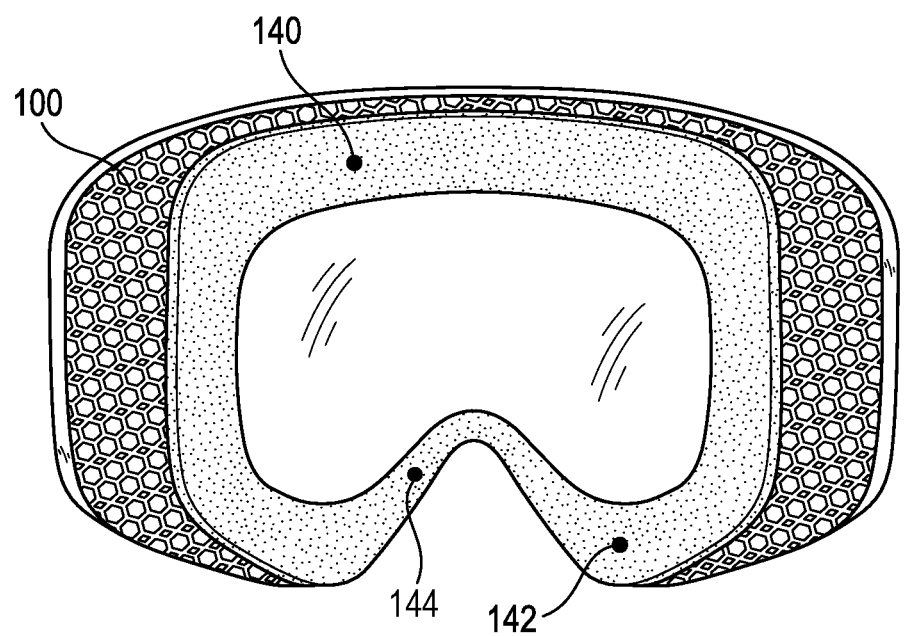
FIG. 7 is a rear view of the goggle of FIG. 1, according to embodiments.

Cushion 100 may be configured to have a different compressibility, or spring force constant, at two or more locations on cushion 100. For example, as shown in FIG. 7, first location 140 may have a first spring force constant and second location 142 may have a second spring force constant that is different from the first spring force constant. As shown in FIG. 7, first location 140 may be located along a brow region of cushion 100 and second location 142 may be located along a cheek region of cushion 100. Different embodiments of cushion 100 may have any number of different locations with different spring force constants (i.e. different compressibility) as desired. For example, first location 140 may have a spring force of between about 0.50 N/mm and about 1.05 N/mm, while second location 142 may have a spring force constant of between about 0.15 N/mm and about 0.50 N/mm. In some embodiments cushion 100 may have a third location 144 with a spring force constant of between about 0.25 N/mm and about 0.75 N/mm. In some embodiments, third location 144 may be located in a nose region of cushion 100.

The spring forces of these three different locations may also be expressed as a percentage of a baseline spring force constant. The baseline spring force constant may be the spring force constant in a region of cushion 100, for example the brow region, or may be an otherwise nominal constant chosen as the baseline. The baseline constant in a region of cushion 100 may be calculated by measuring the spring force constant in the perpendicular direction (as shown by the arrow in FIG. 6) at one or more different locations on the second surface of the selected region of cushion 100 and then, if necessary, averaging those measurements. As used herein, the baseline spring force constant of cushion 100 is set as 100% spring force constant. For example, in some embodiments the spring force constant of first location 140 may be between approximately 100% to approximately 200% of the baseline spring force constant, the spring force constant of second location 142 may be between approximately 80% and approximately 150% of the baseline spring force constant, and the spring force of third location 144 may be between approximately 60% and approximately 130% of the baseline spring force constant. In some embodiments, the spring force constant of first location 140 may be between approximately 120% to approximately 180% of the baseline spring force constant, such as between approximately 140% and approximately 160% of the baseline spring force constant. The spring force constant of second location 142 may be between approximately 90% and approximately 140% of the baseline spring force constant, such as between approximately 100% and approximately 130% of the baseline spring force constant. The spring force of third location 144 may be between approximately 70% and approximately 120% of the baseline spring force constant, such as between approximately 80% and approximately 110% of the baseline spring force constant.

Accordingly, compressibility may vary at any location spaced around the perimeter of cushion 100. In some embodiments, the compressibility remains the same regardless of the depth of compression. The depth or thickness direction is the direction indicated by the arrow in FIG. 6, which is the direction perpendicular to surface 104 of cushion 100. For example, the first five millimeters of compression at a certain location of cushion 100 would require the same force as the last five millimeters of compression of cushion 100 at the same location. The compression forces are additive, such that the first five millimeters might require, for example 1 newton of total force applied, and the next five millimeters requires an additional 1 newton, for a total of 2 newtons force applied, but constant depthwise compressibility means that the incremental force remains the same. This is constant compressibility with respect to the depth or thickness direction of cushion 100.

Figure 7A:
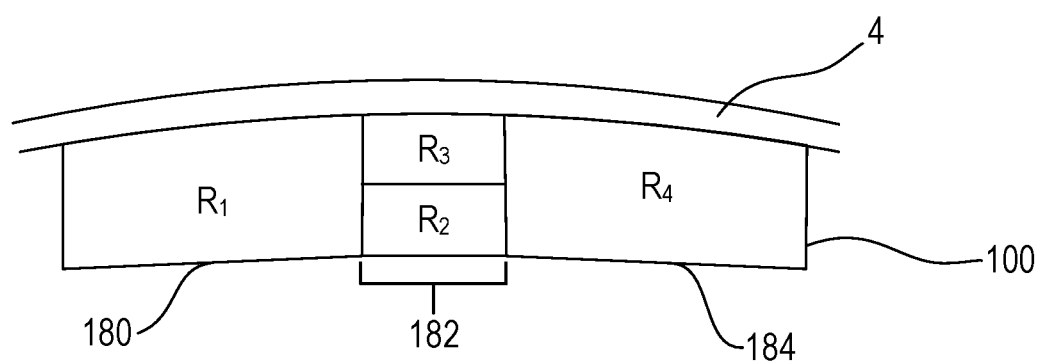
FIG. 7a is a schematic top view of a portion of a goggle according to embodiments.

However, in some embodiments it may be desirable to vary the compressibility in the thickness direction. Varying the compressibility in the thickness direction may be desirable, for example, to allow for portions of cushion 100 to have a higher initial compressibility, which would then feel "softer" to a user. In embodiments of cushion 100 with such variable compression, the incremental force necessary to compress the cushion a set distance changes as the cushion is compressed. For example, compression of the first five millimeters might require a total of 1 newton, but compression of the next five millimeters of cushion 100 might require a total force of 3 newtons, which means that the incremental force to compress the second set of five millimeters of cushion 100 doubled from 1 newton to 2 newtons. This example is illustrated in FIG. 7a, which shows a schematic top view of a portion of cushion 100 and lens 4. This schematic shows cushion 100 in block form with a left section 180, center section 182, and right section 184 representing different portions of cushion 100 having different spring force constants R1, R2, R3, and R4. As shown in center section 182, the portion of cushion 100 nearest the lens may have a constant R3 while the portion of cushion 100 farthest from the lens may have a constant R2 that is different than rate R3. Thus, as center section 182 of the schematic cushion 100 is compressed, compressibility is initially one value that corresponds to R2. Once center section 182 of cushion 100 shown in FIG. 7a is compressed a certain distance, the compressibility changes to a value corresponding to R3.

Some embodiments of cushion 100 may have variable compressibility both laterally or around the perimeter of cushion 100 (as discussed above regarding locations 140 and 142) and in the thickness direction, while other embodiments may only have variable compressibility either laterally or in the thickness direction. In portions of cushion 100 that have varying compressibility in the thickness direction, the compressibility of cushion 100 may then decrease (cushion 100 gets stiffer) as cushion 100 is compressed, which allows for the cushion to give more support to the user and can prevent cushion 100 from bottoming out, when cushion 100 becomes fully compressed.

Further, some embodiments of cushion 100 can be configured with some locations having variable compressibility in the thickness direction, while other locations have a constant compressibility in the thickness direction. This is shown, for example, in FIG. 7a, where the sections of cushion 100 labeled R1 and R4 may have a constant depthwise compressibility, but have different compressibilities than either portion of an adjacent section, such as center section of cushion 100 (i.e. R2 and R3).

Figure 8:
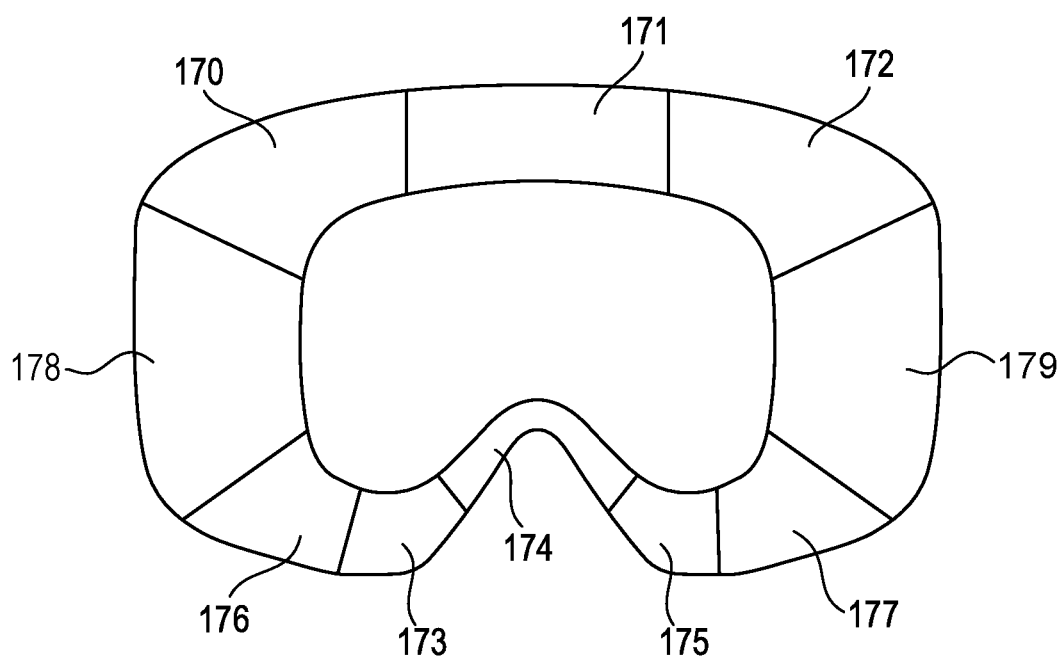
FIG. 8 is a schematic view of the goggle cushion of FIG. 1, according to embodiments.

In some embodiments, the different compressibility may be distributed in separate zones of cushion 100, as best shown in the schematic cushion of FIG. 8. For example, cushion 100 may be separated into a right brow zone 170, center brow zone 171, left brow zone 172, right outer cheek zone 176, right inner cheek zone 173, nose zone 174, left inner cheek zone 175, and left outer cheek zone 177 as shown in FIG. 8. Each of these zones of cushion 100 may have a constant compressibility throughout the zone. The compressibility of each zone may be different than the compressibility of any or all of the other zones or can be approximately the same as one or more of the other zones. The zones discussed here and shown in FIG. 8 are exemplary only, and there may be any number of zones configured to cover any part of cushion 100. The transition from the compressibility of one zone to another zone may be either gradual or discrete. In a gradual transition, the compressibility changes gradually throughout a portion of one or both zones adjacent to the boundary between the zones. The total length of the transition region may be configured as needed to present the desired compressibility transition, and may extend the same or different distances in both of the adjacent zones. In a discrete transition the change from one compressibility to the other constant occurs over a very short distance, and in some embodiments occurs between two adjacent lattice cells 110.

Different compressibilities of a variable compression cushion may be expressed in terms of a percentage of a baseline compressibility or spring force constant. As discussed above, the spring force constants may vary in separate zones of cushion 100 (such as, e.g., the zones shown in the FIG. 8 schematic) to achieve the different compressibilities. The baseline compressibility may be any desired force required to compress the cushion a known distance. In some examples, the baseline compressibility may be selected as the compressibility of a known, constant-compressibility face cushion (where spring force constant is the same throughout the cushion) or the compressibility corresponding to a nominal uniform face pressure to be achieved when a user wears the face cushion. For example, in some embodiments of cushion 100, a spring force constant that requires 0.5 psi for a 5 mm compression depth may be set as the baseline (corresponding to 100%). As a nonlimiting example according to some embodiments, with reference to the FIG. 8 schematic, the spring constants (relative to this baseline) of the different zone of cushion 100 may be as shown below in Table 1.

TABLE 1

| Zone | Spring Force Constant (Percentage of Spring Force Constant Baseline) |
| --- | --- |
| Right Brow Zone 170 | 175% |
| Center Brow Zone 171 | 175% |
| Left Brow Zone 172 | 175% |
| Right Outer Cheek Zone 176 | 125% |
| Right Inner Cheek Zone 173 | 110% |
| Nose Zone 174 | 60% |
| Left Inner Cheek Zone 175 | 110% |
| Left Outer Cheek Zone 177 | 125% |

The different compressibilities (or spring force constants) in the various zones of cushion 100 may also be shown as a percentage normalized to the compressibility (or spring force constant) of a selected zone. As a non-limiting example according to some embodiments, Table 2 shows the different spring force constants (and hence compressibilities) of the zones of cushion 100 relative to the spring force constant of center brow zone 171 taken as the baseline (corresponding to 100%). Thus, in these embodiments, cushion 100 can have brow zones 170, 171, 172 that are about 30-40% stiffer (or less compressible) than the cheek zones 173, 175, 176, 177, and the nose zone 174 can be about half as stiff (or about twice as compressible) as the cheek zones.

TABLE 2

| Zone | Spring Force Constant (Percentage of Baseline Center Brow Zone 171) |
| --- | --- |
| Right Brow Zone 170 | 100% |
| Center Brow Zone 171 | 100% |
| Left Brow Zone 172 | 100% |
| Right Outer Cheek Zone 176 | 70% |
| Right Inner Cheek Zone 173 | 60% |
| Nose Zone 174 | 35% |
| Left Inner Cheek Zone 175 | 60% |
| Left Outer Cheek Zone 177 | 70% |

As another nonlimiting example according to some embodiments, Table 3 shows the different spring force constants (and hence compressibilities) of the zones of cushion 100 relative to the spring force constant of center brow zone 171 taken as the baseline (corresponding to 100%). In some embodiments, this baseline (e.g. center brow zone 171 in the embodiment of Table 3) can correlate to approximately 3.4 psi for about a 5 mm compression depth. Thus, in these embodiments, cushion 100 can have brow zones 170, 171, 172 that are about 30-55% stiffer (or less compressible) than the cheek zones 173, 175, 176, 177, which can be about 15-35% stiffer (or less compressible) than the nose zone 174. Further, in some embodiments, the lateral side regions 178 and 179 of cushion 100 can be zones for transitioning the compressibility from low in the brow to high in the cheek and nose. For example, the lower portion of lateral side regions 178 and 179 of cushion 100 can be highly compressible with a compressibility closer to the cheek zone, for example about 70% the stiffness of the brow zones. In some embodiments, the upper portion of the lateral side regions 178 and 179 can have compressibility closer to the brow zones, for example, about 85-95% the stiffness of the brow zones.

TABLE 3

| Zone | Spring Force Constant (Percentage of Baseline) |
| --- | --- |
| Right Brow Zone 170 | 118% |
| Center Brow Zone 171 | 100% |
| Left Brow Zone 172 | 118% |
| Right Outer Cheek Zone 176 | 85% |
| Right Inner Cheek Zone 173 | 70% |
| Nose Zone 174 | 55% |
| Left Inner Cheek Zone 175 | 70% |
| Left Outer Cheek Zone 177 | 85% |

It should be appreciated that any of the zone spring constants may serve as baseline for arriving at a percent relative spring constant between zones. Thus, with reference to Table 3, the relative compressibilities in the various zones of cushion 100 may also be characterized as a percentage normalized to the compressibility of the brow zone 170 or 172 serving as baseline. In such case, then the relative spring constant of outer cheek zones 176, 177 can be about 70%, the inner cheek zones 173, 175 can be about 60%, the center brow zone 171 can be about 85%, and the nose zone 174 can be about 45% of the baseline. In still other embodiments of cushion 100, with reference to the zones of FIG. 8 and assuming, e.g., brow zone 170 or 172 serves as baseline, then the relative spring constant of outer cheek zones 176, 177 can be between about 40% to about 100%, such as between about 50% to about 90%, such as between about 60% to about 80%, about 70%, or about 75% of the baseline. Inner cheek zones 173, 175 can be between about 30% to about 90%, such as between about 40% to about 80%, such as between about 50% to about 70%, about 60% or about 65% of the baseline. Nose zone 174 can be between about 15% to about 75%, such as between about 25% to about 65%, such as between about 35% to about 55%, about 45%, about 50% or about 55% of the baseline. Thus, in some embodiments of variable compression (e.g., cushion 100), the brow zone 170 or 172 can require about 3.5 psi for about a 5 mm compression depth, whereas, for the same compression depth, outer cheek zones 176, 177 can require about 2.6 psi, inner cheek zones 173, 175 can require about 2.3 psi, and nose zone 174 can require about 1.8 psi. As discussed above, the relative spring force constants (or compressibilities) can correspond with relative face pressures between zones of cushion 100. Thus, as mentioned previously, varying spring force constants (or compressibility) in the different zones can achieve a comfortable face pressure in respective zones, and a comfortable fit of the goggle.

Zones of different compressibility of a variable compression cushion may correspond to different face pressures experienced by the user where cushion 100 contacts the face. Facial geometry and goggle design means that cushion 100 will be compressed to different depths at different points or zones of cushion 100. Goggle cushions with constant compressibility results in a greater compression force on the face of a wearer in an area where the cushion is compressed a greater depth than other areas, which can be uncomfortable. However, variable compression cushion embodiments of the present disclosure can be designed to have higher compressibility in such areas so that such compression force on the face is not as great despite the greater compression depth. For example, Table 4 shows the face pressures experienced by a user while wearing some embodiments of goggle 1 with a variable compression cushion 100.

TABLE 4

Exemplary Face Pressure by Zone

| Zone | Face Pressure (psi) |
| --- | --- |
| Right Brow Zone 170 | 1.00 to 2.05 |
| Center Brow Zone 171 | 0.540 to 0.750 |
| Left Brow Zone 172 | 1.00 to 2.05 |
| Right Outer Cheek Zone 176 | 0.75 to 1.10 |
| Right Inner Cheek Zone 173 | 0.60 to 1.01 |
| Nose Zone 174 | 0.55 to 0.71 |
| Left Inner Cheek Zone 175 | 0.60 to 1.01 |
| Left Outer Cheek Zone 177 | 0.75 to 1.10 |

Similar to the discussion above with respect to spring force constants and compressibility, the face pressures corresponding to the different zones of a variable compression cushion may be expressed as a percentage of a baseline face pressure. In some embodiments, the baseline face pressure may be selected as a nominal uniform pressure that would be created by wearing a conventional chassis goggle system with frame and cushion combination. For example, a baseline face pressure may be between 0.50 psi and 0.90 psi, in some embodiments.

A baseline face pressure may also be set as the face pressure in a single zone where cushion 100 contacts the face. For example, in some embodiments the baseline face pressure may be set as the face pressure in center brow zone 171. In these embodiments, the face pressure in right brow zone 170 or left brow zone 172 may be between two to three times the baseline face pressure. In these embodiments, for example, the face pressure in nose zone 174 may be between one to two times the baseline face pressure. In these embodiments, for example, the face pressure in right inner cheek zone 173 or left inner cheek zone 175 may be between one to two times the baseline face pressure. In these embodiments, for example, the face pressure in right outer cheek zone 176 or left outer cheek zone 177 may be between one to two times the baseline face pressure.

It should be appreciated that any of the zone pressures shown in Table 4 may serve as a baseline face pressure for arriving at relative face pressures between zones, expressed in percent relative to the baseline. For example, with reference to Table 4, assuming right or left brow zones 170 or 172 serve as the baseline, with a face pressure of 1.0 PSI, then the relative face pressure of outer cheek zones 176, 177 can be between about 75% to 110%. The relative face pressure of inner cheek zones 173, 175 can be between about 60% to about 101%. The relative face pressure of nose zone 174 can be between about 55% to about 71%. As another non-limiting example, assuming left or right brow zone 170, 172 are selected as the baseline with a 2.05 psi face pressure, center brow zone 171 can be between about 25% to about 35%. The relative face pressure of outer cheek zones 176 and 177 can be between about 35% to about 55%. The relative face pressure of inner cheek zones 173 and 175 can be between about 30% to about 50%. The relative face pressure of nose zone 174 can be between about 25% to about 35%. The relative face pressures can correspond with relative compressibility between zones of the cushion 100. Thus, as mentioned previously, varying compressibility in the different zones can achieve a comfortable face pressure in respective zones, and a comfortable fit of the goggle.

For another example, Table 5 shows the face pressures experienced by a user while wearing an embodiment of goggle 1 with a variable compression cushion 100, with either the right or left brow zones 171, 172 serving as the baseline. As a nonlimiting example, in some embodiments, this baseline can correlate to approximately 2.4 psi.

TABLE 5

| Zone | Face Pressure (Percentage of Baseline) |
| --- | --- |
| Right Brow Zone 170 | 100% |
| Center Brow Zone 171 | 30% |
| Left Brow Zone 172 | 100% |
| Right Outer Cheek Zone 176 | 45% |
| Right Inner Cheek Zone 173 | 45% |
| Nose Zone 174 | 30% |
| Left Inner Cheek Zone 175 | 45% |
| Left Outer Cheek Zone 177 | 45% |

Another advantage of embodiments of the present disclosure is the ability to vary compression while independently designing the thickness of cushion 100. The thickness of cushion 100 is an important design parameter because it directly affects the distance between the inside of lens 4 and the face of the user—commonly known as the standoff distance, and measured from the lens to the edge of cushion 100 as shown by measurement d in FIG. 3. This standoff distance must not be too close or too far for aesthetic and lens performance reasons. Therefore, it is desirable to maintain a target thickness of cushion 100 in different parts of cushion 100. Since changing the compressibility of cushion 100 is a function of the parameters of the lattice structure of cushion 100, and not the total thickness of cushion 100, adjacent areas of cushion 100, for example right brow zone 170 and center brow zone 171, may have the same thickness while having different compressibility. This allows for a better fit to the user's face and ensures ideal and continuous contact between cushion 100 and the user's face around the full perimeter of cushion 100. This allows a designer to tailor the compressibility of cushion 100 while still allowing the designer to select a broad range of thickness of cushion 100, which further improves the fit and comfort of cushion 100 and goggle 1.

Figure 9:
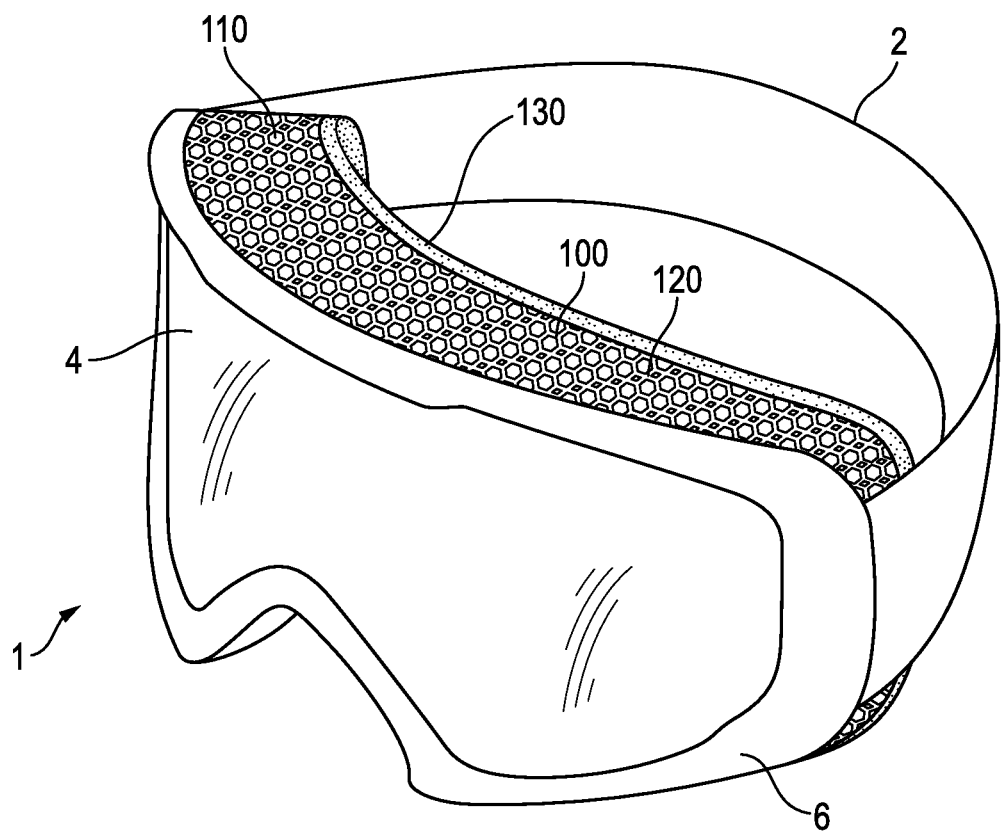
FIG. 9 is a perspective view of a goggle, according to embodiments.
Figure 10:
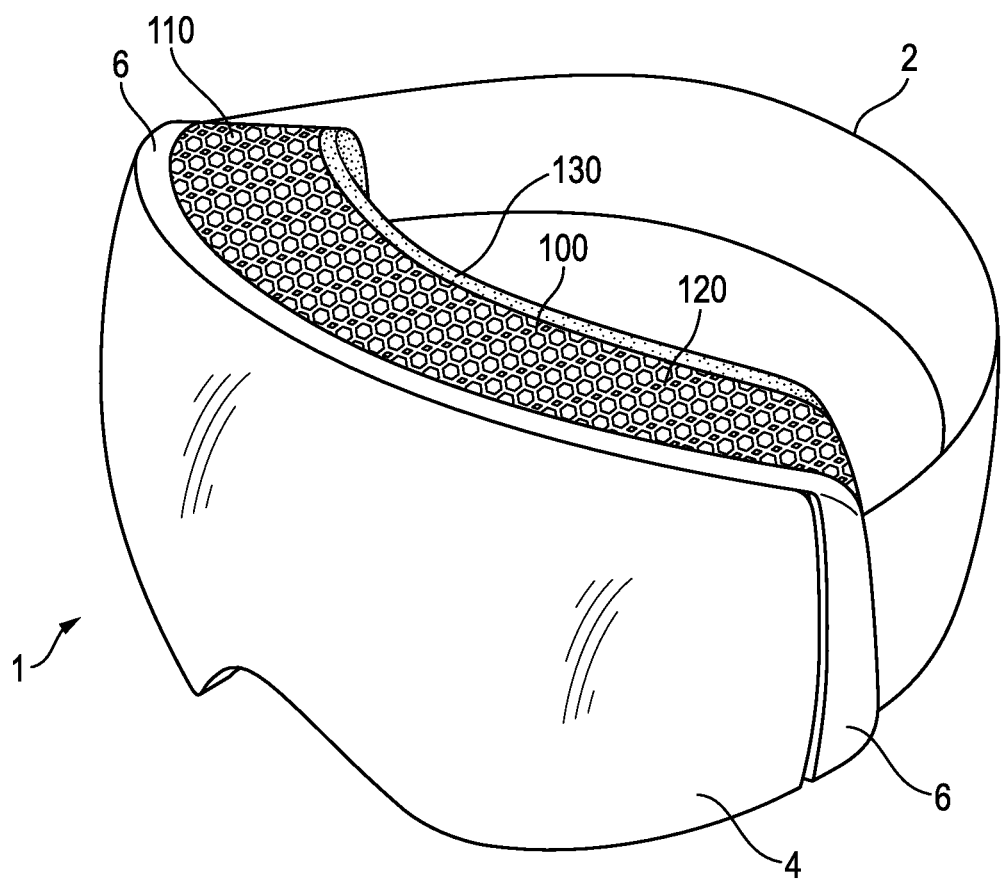
FIG. 10 is a perspective view of a goggle, according to embodiments.

Cushion 100 may be used with a range of different types of goggles. For example, goggle 1 of FIGS. 1-4 shows a frameless goggle, where both cushion 100 and strap 2 are directly attached to lens 4. Cushion 100 may also be used with goggle 1 that includes a frame 6, as shown in FIGS. 9 and 10, for example. FIG. 9 shows a perspective view of goggle 1 with frame 6 disposed around lens 4. FIG. 10 shows a perspective view of a "rimless" type goggle 1 with frame 6 disposed on the interior side of lens 4. In both of these types of goggles 1, cushion 100 may be attached directly to frame 6 instead of lens 4. Cushion 100 is otherwise unchanged from the embodiments of cushion 100 discussed above and may include any or all features discussed above. Cushion 100 may also be adapted for use with any other kind of eyewear that employs a cushion to contact the face of the user.

Another aspect of the design of cushion 100 is ventilation. Ventilation of the interior surface of lens 4 is important to minimize condensation buildup on lens 4—more commonly known as "fogging" of lens 4. Ventilation is particularly important in "closed loop" embodiments of cushion 100 such as those shown in FIGS. 1-4 because cushion 100 forms an enclosed area bounded by lens 4, the face of the user, and cushion 100. Without proper ventilation, this area can increase in temperature and humidity, which contributes to lens fogging and discomfort for the user.

Figure 13:
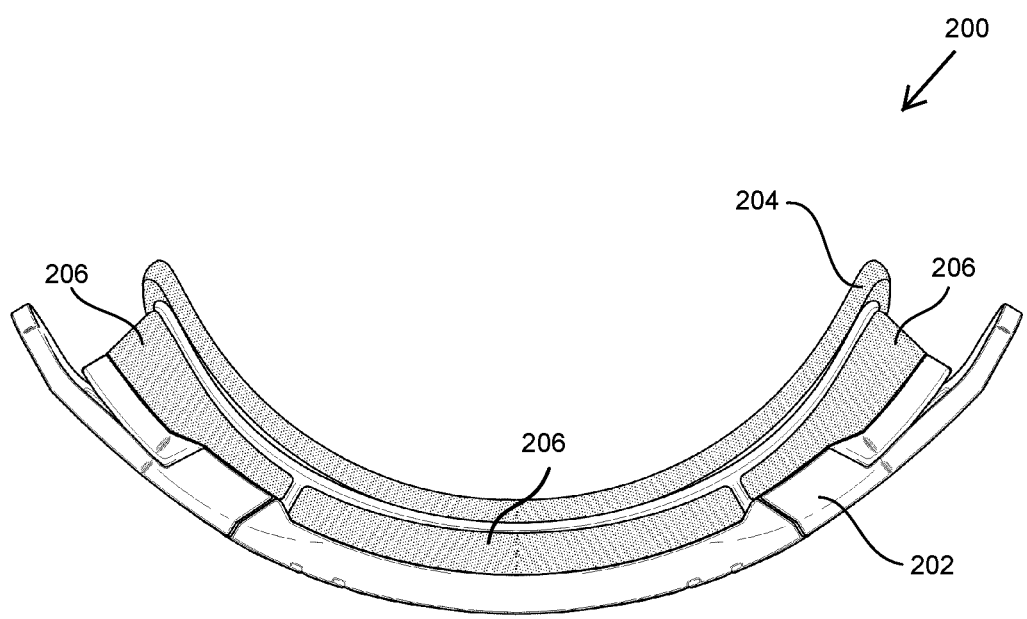
FIG. 13 is a top view of a prior art google.

Traditionally, goggle cushions are made out of foam material that allows minimal airflow through the cushion. As shown in FIG. 13, ventilation of the lens of a traditional goggle 200 is typically accomplished using openings or gaps 206 in a frame 202 holding the lens. These openings 206 are typically covered with a porous foam material that allows for ventilation. This approach requires additional complexity in the design of the frame and does not allow for ventilation through the entire area between the lens and the user's face because of the construction of traditional cushion 204. Further, this approach is difficult to implement using frameless goggles because there is no frame to accommodate holes or other venting structures.

The lattice structure of cushion 100 can pass air through cushion 100 because of the open nature of lattice cells 110, which allows air to flow through lattice cells 110 and thus through cushion 100. Therefore, cushion 100 is able to ventilate lens 4 with much greater efficiency than a traditional cushion (i.e. traditional cushion 204), which is usually constructed of foam material that provides minimal (and in some cases effectively zero) ventilation. This is due to the much larger size range of lattice cells 110.

Figure 3:
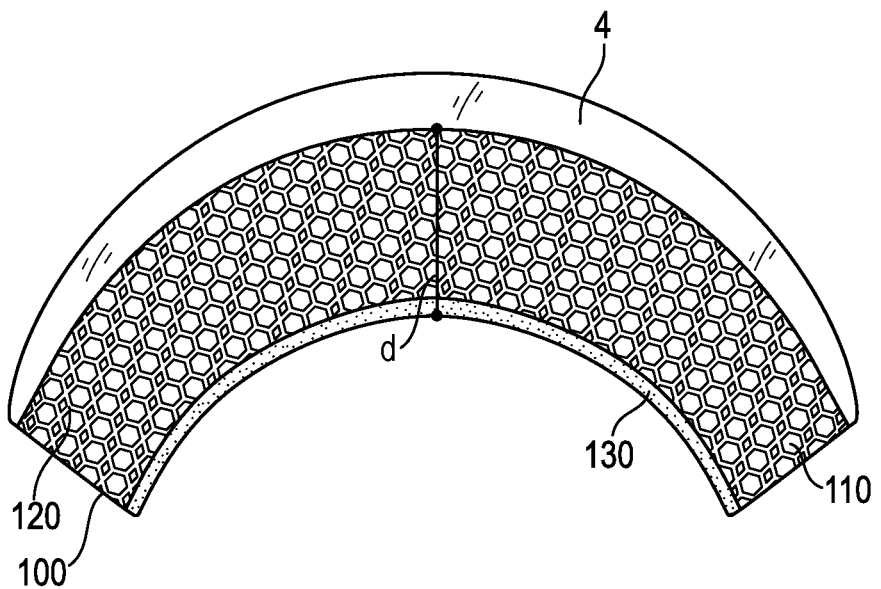
FIG. 3 is a top view of the goggle of FIG. 1, according to embodiments.
Figure 4:
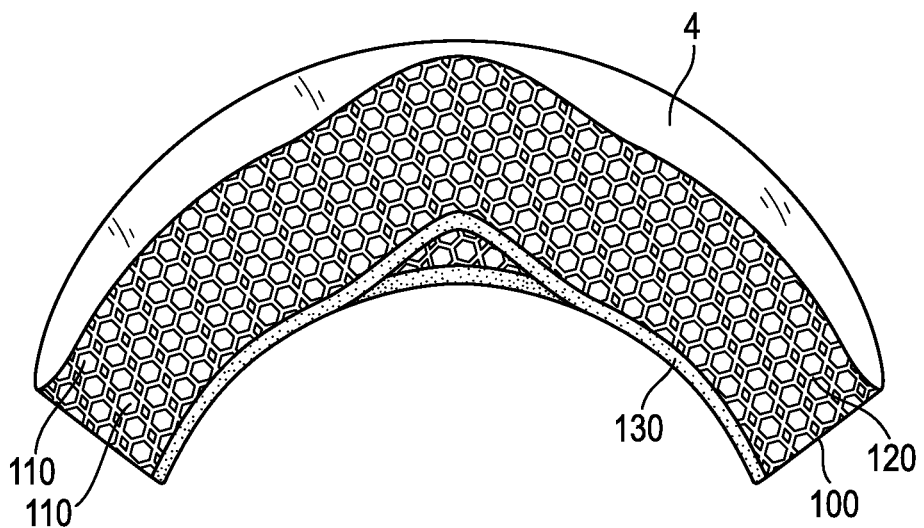
FIG. 4 is a bottom view of the goggle of FIG. 1, according to embodiments.

Accordingly, in some embodiments, the ventilation area provided by cushion 100 is more than the ventilation area of a similarly configured goggle 1 with a standard foam cushion. In some embodiments, the ventilation area provided by cushion 100 may be two times or more, from two to three times more, or three times or more than the ventilation area of a similarly configured goggle 1 with a standard foam cushion. This increase in ventilation area would result in a similar increase in total airflow of two times or more. This improvement occurs when cushion 100 is used with both frameless goggles and goggles with frames. In frameless goggles, where cushion 100 is directly attached to lens 4, this improvement in ventilation area may be even greater than the result discussed above because of the increased thickness of cushion 100 as compared to embodiments of cushion 100 attached to a frame. For example, a standard goggle 200 with a constant-compressibility cushion 204 attached to a frame 202 may have a ventilation area of approximately 1500 mm$^2$, while the same goggle with cushion 100 designed with approximately the same lens to face standoff distance d at a given location (e.g. the distance d from a location on the rear surface of lens 4 and on the centerline of lens 4 to the face of the user as shown in FIG. 3) as the known goggle may have a ventilation area of approximately 4500 mm$^2$. This substantial increase in cushion area allows goggle 1 to have much more ventilation area for the same cushion thickness, and thus distance from the face of the user. Alternatively, the same ventilation area as a conventional goggle using a conventional foam cushion can be achieved with a thinner cushion 100, which allows goggle 1 to be fitted closer to the face of a user. The improvement in ventilation may be greater for frameless goggles is because the entire area of cushion 100 between the face of the wearer and lens 4 allows for ventilation.

Figure 11:
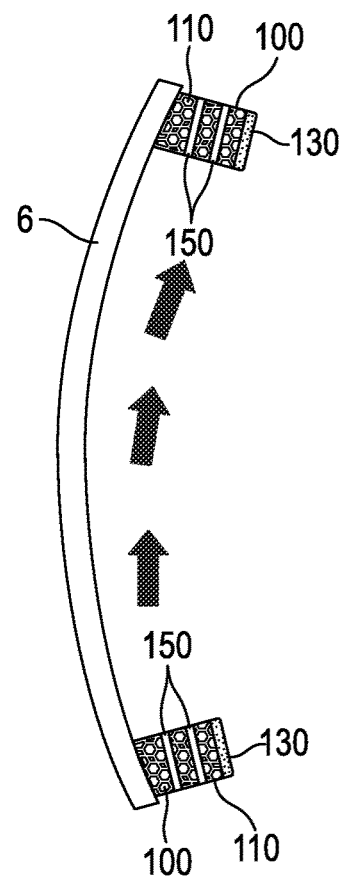
FIG. 11 is a cross-section view of a goggle, along line 11-11 of FIG. 2 according to embodiments.

Further, in some embodiments cushion 100 may be configured to enhance ventilation of the enclosed space formed by lens 4 and cushion 100. Specifically, as best shown in FIG. 11, cushion 100 may include ventilation channels 150 incorporated into the lattice structure of cushion 100. Ventilation channels 150 may be openings that pass through cushion 100 to improve airflow from the exterior of cushion 100 to the interior of cushion 100. As shown in FIG. 11, embodiments of ventilation channel 150 may extend in a substantially vertical direction. There may be more than one ventilation channel 150 spaced either evenly or irregularly throughout cushion 100. In some embodiments, ventilation channels 150 may be configured to direct airflow in a desired direction across lens 4. For example, ventilation channels 150 may be positioned to route airflow from the nose and cheek regions of cushion 100 upwards across lens 4 to exit through the brow region, as shown by the arrows in FIG. 11. This airflow can aid in reducing fogging of lens 4 by bringing cooler, dryer air across the rear surface of lens 4. Ventilation channels 150 may also be configured to enhance user comfort, for example by increasing the exchange of air in the enclosed space formed by lens 4 and cushion 100, which can result in a lower air temperature in the enclosed space. In some embodiments, ventilation channels 150 are configured to route airflow across the surface of lens 4 while keeping the airflow routed away from the face of the user. For example, ventilation channels 150 may be angled to route airflow towards the lens and way from the face of the user. This routing may enhance user comfort by minimizing the airflow across the face of the user (e.g. if the airflow is very cold) while still enhancing performance of lens 4 by reducing fogging as described above. In other embodiments, ventilation channels 150 may be concentrated in an area proximate to lens 4, and thus increase ventilation nearest to the rear surface of lens 4 and farthest from the face of the user. The specific dimensions, orientation, and distribution of ventilation channels 150 may be implemented in any desired manner to enhance airflow and ventilation.

Figure 12:
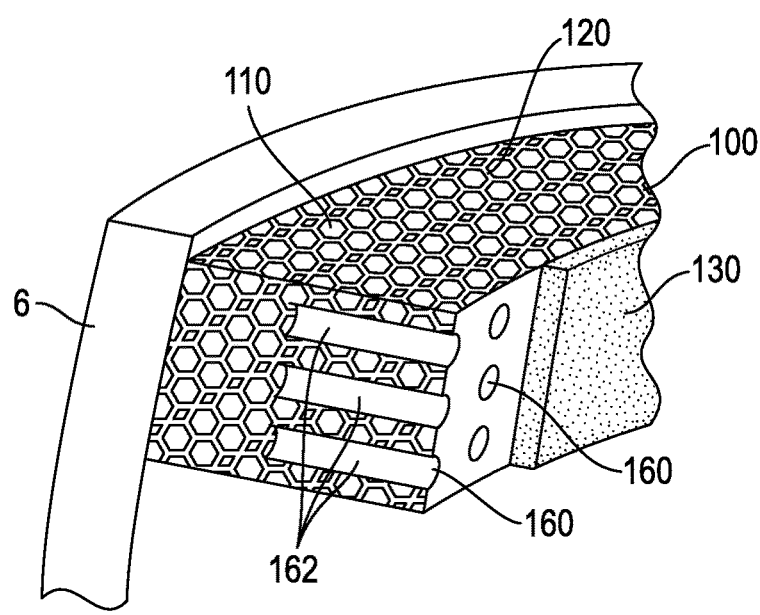
FIG. 12 is a cross-section view of the goggle cushion of FIG. 1, according to embodiments.

A further aspect of some embodiments relates to moisture management. A user of goggle 1 might perspire. Traditional goggle cushions will generally absorb the perspiration of a user and remain damp or wet while the moisture slowly evaporates. This can be uncomfortable for the user and can contribute to increased humidity in the interior of lens 4, which can increase lens fogging. In some embodiments, cushion 100 can include structures to improve moisture management by transporting moisture away from the face of the user and by improving evaporation of the moisture. As shown in FIG. 12, embodiments of cushion 100 can include holes 160 in second surface 104. These holes 160 are fluidly connected to moisture management channels 162. As shown in FIG. 12, face layer 130 covers surface 104 and holes 160. In these embodiments of goggle 1, face layer 130 will be configured to quickly transport moisture through face layer 130. Once the moisture reaches second surface 104 it travels through holes 160 and into moisture management channels 162. Moisture management channels 162 are configured to be at least partially exposed to the airflow through cushion 100. Thus, moisture is transported through holes 160 and is then exposed to airflow in cushion 100 by moisture management channels 162. The airflow through cushion 100 improves evaporation of the moisture in moisture management channels 162. Holes 160 and moisture management channels 162 may be designed with any desired dimensions and distributed as desired throughout cushion 100. In some embodiments holes 160 and moisture management channels 162 may be concentrated in high moisture areas, for example along the brow.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. When either ranges of values or specific values are used, the ranges or specific values are approximate. Specifically, values and ranges used in any of the above Tables should be understood to be approximate. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A goggle, comprising:
a cushion having a first surface and a second surface opposite the first surface, the second surface of the cushion opposite the first surface is configured to follow a contour of a face of a user when the goggle is being worn, wherein the cushion comprises a continuous and uninterrupted lattice structure,
a face layer attached to the second surface of the cushion, wherein the cushion has a first zone with a first compressibility,
wherein the cushion has a second zone with a second compressibility that is greater than the first compressibility, the second zone being adjacent to the first zone, and
wherein the second surface comprises holes configured to fluidly connect the second surface with an interior of the cushion, and
wherein the lattice structure comprises moisture management channels configured to transport moisture from the holes through the lattice structure to remove the moisture.

2. The goggle of claim 1, wherein the compressibility of the cushion varies in a gradual transition between the first zone and the second zone, and
wherein the first zone is located in a brow region of the cushion that is configured to contact a brow of a user when the goggle is being worn, and wherein the second zone is located in a cheek region of the cushion that is configured to contact a cheek of a user when the goggle is being worn.

3. The goggle of claim 2, wherein the cushion has a third zone with a third compressibility greater than the second compressibility, wherein the third zone is located in a nose region of the cushion that is configured to contact the nose of a user when the goggle is being worn.

4. The goggle of claim 3, wherein a baseline face pressure of the cushion is a face pressure in the first zone,
wherein a face pressure in the second zone is between approximately 30% to approximately 80% of the baseline face pressure, and
wherein a face pressure in the third zone is between approximately 25% to approximately 80% of the baseline face pressure.

5. The goggle of claim 1, wherein a spring force constant of the cushion as measured in a direction perpendicular to the second surface varies with a depth of compression.

6. The goggle of claim 1, further comprising a frame configured to support a lens, wherein the first surface is configured to attach to the frame.

7. The goggle of claim 1, wherein the cushion has a vented area that is between two to three times a vented area of a goggle with a foam constant-compressibility cushion and a face standoff distance that is the same as the goggle of claim 1.

8. The goggle of claim 1, wherein the cushion comprises venting channels that are configured to direct airflow from outside of a loop formed by the cushion to inside the loop formed by the cushion.

9. The goggle of claim 1, wherein a baseline face pressure of the cushion is a face pressure in the first zone, and
wherein a face pressure in the second zone is between approximately 30% to approximately 80% of the baseline face pressure.

10. The goggle of claim 1, wherein the lattice structure is additively manufactured.

11. The goggle of claim 1, wherein a characteristic of the lattice structure corresponding to a compressibility of the cushion varies between the first zone and the second zone.

12. A goggle, comprising:
a cushion having a first surface and second surface opposite the first surface, the second surface of the cushion opposite the first surface is configured to follow a contour of a face of a user when the goggle is being worn,
a face layer attached to the second surface of the cushion, wherein the cushion comprises an additively manufactured, continuous and uninterrupted lattice structure,
wherein the cushion is configured to create a first pressure on the face of the user in a first zone when the goggle is being worn, the first zone having a first compressibility,
wherein the cushion is configured to create a second pressure on the face of the user in a second zone separate from the first zone when the goggle is being worn, the second zone having a second compressibility different from the first compressibility,
wherein the second pressure is different from the first pressure,
wherein the second surface comprises holes configured to fluidly connect the second surface with an interior of the cushion, and
wherein the lattice structure comprises moisture management channels configured to transport moisture from the holes through the lattice structure to remove the moisture.

13. The goggle of claim 12, wherein the first zone is located along a brow region of the cushion and the second zone is located along a cheek region of the cushion, and
wherein the first pressure is greater than the second pressure.

14. The goggle of claim 13, wherein the cushion is configured to create a third pressure on the face of the user in a third zone separate from the first and second zones when the goggle is being worn, wherein the third pressure is different from at least one of the first pressure and the second pressure.

15. The goggle of claim 14, wherein the third zone is located along a nose region of the cushion.

16. The goggle of claim 12, wherein the second zone and the first zone are adjacent to each other, and wherein the cushion is configured to have a gradual transition between the second pressure and the first pressure through the regions of the second and first zones immediately adjacent to each other.

17. The goggle of claim 12, further comprising a frame configured to support a lens, wherein the cushion is configured to attach to the frame.

18. The goggle of claim 12, wherein the cushion has a vented area that is between two to three times a vented area of a goggle with a foam constant-compressibility cushion and a face standoff distance that is the same as the goggle of claim 12.

19. The goggle of claim 12, wherein the cushion comprises venting channels that are configured to direct airflow from outside of a loop formed by the cushion to inside the loop formed by the cushion.

20. The goggle of claim 12, wherein the cushion forms a closed loop on an interior surface of the goggle.

21. A goggle, comprising:
a lens;
a cushion comprising a continuous and uninterrupted lattice structure comprising a plurality of lattice cells, a first surface of the cushion configured to mate with a portion of the goggle;

a second surface of the cushion opposite the first surface, wherein first and second spring force constants at first and second locations, respectively, on the second surface are different, where the first and second spring force constants are measured in a direction extending between the first surface and the second surface, a plurality of holes disposed in the second surface, wherein the holes fluidly connect the second surface with an interior of the cushion; and a plurality of moisture management channels in the lattice structure configured to transport moisture from the holes through the lattice structure to remove the moisture, wherein the cushion is disposed adjacent to an interior surface of the lens.

22. The goggle of claim 21, further comprising a frame to support the lens, wherein the cushion is attached to an interior surface of the frame.

23. The goggle of claim 21, wherein the cushion further comprises a third spring force constant that is different from the first and second spring force constants at a third location on the second surface.

24. The goggle of claim 23, wherein the first location is located in a brow region of the cushion, the second location is located in a cheek region of the cushion, and the third location is located in a nose region of the cushion.

25. The goggle of claim 24, wherein the first spring force constant is between approximately 100% to approximately 200% of an average baseline spring force constant of the entire cushion, the second spring force constant is between approximately 80% and approximately 150% of the average baseline spring force constant, and the third spring force constant is between approximately 60% and approximately 130% of the average baseline spring force constant.

26. The goggle of claim 21, further comprising:
a face layer attached to the second surface, wherein the face layer covers the entire second surface.

27. The goggle of claim 26, wherein the lattice structure is at least twice the thickness of the face layer.

28. The goggle of claim 21, wherein the lattice structure further comprises airflow channels that are configured to direct airflow from outside of a loop formed by the cushion to inside the loop formed by the cushion.

29. The goggle of claim 21, wherein the cushion has a vented area.

30. The goggle of claim 21, wherein the transition between the first and second spring constants is gradual.

31. A goggle, comprising:
a cushion having a first surface and a second surface opposite the first surface, the second surface of the cushion opposite the first surface is configured to follow a contour of a face of a user when the goggle is being worn, wherein the cushion comprises a continuous and uninterrupted lattice structure, wherein the cushion has a first zone with a first compressibility, wherein the cushion has a second zone with a second compressibility that is greater than the first compressibility, the second zone being adjacent to the first zone, wherein a baseline face pressure of the cushion is a face pressure in the first zone, and wherein a face pressure in the second zone is between approximately 30% to approximately 80% of the baseline face pressure, and wherein the compressibility of the cushion varies in a gradual transition between the first zone and the second zone.

32. A goggle, comprising:
a lens;
a cushion comprising a continuous and uninterrupted lattice structure comprising a plurality of lattice cells,
a first surface of the cushion configured to mate with a portion of the goggle; and
a second surface of the cushion opposite the first surface, wherein first and second spring force constants at first and second locations, respectively, on the second surface are different, where the first and second spring force constants are measured in a direction extending between the first surface and the second surface, wherein the cushion is disposed adjacent to an interior surface of the lens, and wherein the first spring force constant is between approximately 100% to approximately 200% of an average baseline spring force constant of the entire cushion, and the second spring force constant is between approximately 80% and approximately 150% of the average baseline spring force constant.

* * * * *